United States Patent [19]
Popp et al.

[11] Patent Number: 5,683,752
[45] Date of Patent: Nov. 4, 1997

[54] APPARATUS AND METHODS FOR SELECTIVELY CONTROLLING A SPRAY OF LIQUID TO FORM A DISTINCT PATTERN

[75] Inventors: Robert Lee Popp, Hortonville; Michael Lee Barlament, Appleton; Larry Dean Primeau, DePere, all of Wis.

[73] Assignee: Kimberly-Clark Worldwide, Inc., Neenah, Wis.

[21] Appl. No.: 442,923

[22] Filed: May 17, 1995

Related U.S. Application Data

[62] Division of Ser. No. 991,780, Dec. 16, 1992.

[51] Int. Cl.$^6$ ..................... B05D 7/00
[52] U.S. Cl. ............... 427/421; 427/8; 427/282; 118/668; 118/669; 118/672; 118/676; 118/679; 118/684
[58] Field of Search ............ 118/668, 669, 118/672, 676, 679, 684, 315; 427/8, 421, 282

[56] References Cited

U.S. PATENT DOCUMENTS

| Re. 33,481 | 12/1990 | Ziecker et al. | 239/298 |
|---|---|---|---|
| 3,219,276 | 11/1965 | Norris | 118/315 |
| 3,402,695 | 9/1968 | Baker et al. | 118/315 |
| 3,452,710 | 7/1969 | Hentschel | 118/315 |
| 3,584,571 | 6/1971 | Schmoll | 118/315 |
| 3,661,679 | 5/1972 | Law | 156/356 |
| 4,058,991 | 11/1977 | McCollough | 118/314 |
| 4,170,883 | 10/1979 | Varner | 118/314 |
| 4,237,539 | 12/1980 | Piovoso et al. | 364/552 |

(List continued on next page.)

FOREIGN PATENT DOCUMENTS

| 1057457 | 7/1979 | Canada. |
|---|---|---|
| 1058125 | 7/1979 | Canada. |
| 1063918 | 10/1979 | Canada. |
| 1065554 | 11/1979 | Canada. |
| 1287700 | 8/1981 | Canada. |
| 1111630 | 11/1981 | Canada. |
| 1122509 | 4/1982 | Canada. |
| 1148701 | 6/1983 | Canada. |
| 1153152 | 9/1983 | Canada. |
| 1157641 | 11/1983 | Canada. |
| 1175602 | 10/1984 | Canada. |
| 1177633 | 11/1984 | Canada. |
| 1182601 | 2/1985 | Canada. |
| 1183306 | 3/1985 | Canada. |
| 1207104 | 7/1986 | Canada. |
| 1299477 | 10/1986 | Canada. |
| 1245001 | 11/1988 | Canada. |
| 1247803 | 1/1989 | Canada. |
| 1274052 | 9/1990 | Canada. |
| 2013182 | 10/1990 | Canada. |
| 2013905 | 10/1990 | Canada. |
| 1275896 | 11/1990 | Canada. |
| 1277577 | 12/1990 | Canada. |
| 2058421 | 2/1991 | Canada. |
| 1286854 | 7/1991 | Canada. |
| 1288200 | 9/1991 | Canada. |
| 1290502 | 10/1991 | Canada. |
| 1291325 | 10/1991 | Canada. |
| 1294390 | 1/1992 | Canada. |
| 1296489 | 3/1992 | Canada. |
| 1298934 | 4/1992 | Canada. |
| 0111618A2 | 6/1984 | European Pat. Off.. |
| 0380781A2 | 8/1990 | European Pat. Off.. |
| 0445908 | 9/1991 | European Pat. Off.. |
| 0449410 | 10/1991 | European Pat. Off.. |
| 3325126C1 | 1/1985 | Germany. |
| 1575140 | 9/1980 | United Kingdom. |
| 2143320 | 10/1986 | United Kingdom. |
| WO84/02190 | 6/1984 | WIPO. |

*Primary Examiner*—Shrive Beck
*Assistant Examiner*—David M. Maiorana
*Attorney, Agent, or Firm*—Douglas L. Miller

[57] ABSTRACT

Apparatus and methods are disclosed for selectively applying a liquid on a surface in a selected pattern and position on the surface. The apparatus and methods include programmable devices that individually control a plurality of nozzles wherein each nozzle has its own separate liquid supply source.

17 Claims, 8 Drawing Sheets

U.S. PATENT DOCUMENTS

| | | | |
|---|---|---|---|
| 4,239,578 | 12/1980 | Gore | 156/361 |
| 4,264,957 | 4/1981 | Pautzke | 364/469 |
| 4,370,944 | 2/1983 | Ngatu et al. | 118/302 |
| 4,456,374 | 6/1984 | Langberg | 356/237 |
| 4,490,618 | 12/1984 | Cielo | 250/571 |
| 4,528,630 | 7/1985 | Sargent | 364/469 |
| 4,530,862 | 7/1985 | Kerzel | 118/669 |
| 4,532,596 | 7/1985 | Paugsley | 364/469 |
| 4,603,976 | 8/1986 | Fetzer et al. | 356/402 |
| 4,608,115 | 8/1986 | Schroth et al. | 156/519 |
| 4,644,140 | 2/1987 | Hillinger | 219/535 |
| 4,680,205 | 7/1987 | Lerner et al. | 428/29 |
| 4,687,137 | 8/1987 | Boger et al. | 118/315 |
| 4,701,239 | 10/1987 | Craig | 156/519 |
| 4,711,683 | 12/1987 | Merkatoris | 156/164 |
| 4,719,575 | 1/1988 | Gnuechtel | 364/469 |
| 4,757,930 | 7/1988 | Ditto | 226/27 |
| 4,762,582 | 8/1988 | de Jonckheere | 156/164 |
| 4,764,234 | 8/1988 | Smits et al. | 118/323 |
| 4,764,242 | 8/1988 | Gressick et al. | 118/315 |
| 4,769,650 | 9/1988 | Peng et al. | 346/75 |
| 4,774,109 | 9/1988 | Hadzimihalis et al. | 427/286 |
| 4,778,458 | 10/1988 | Gronostajski | 604/366 |
| 4,792,817 | 12/1988 | Barney | 346/140 R |
| 4,795,451 | 1/1989 | Buckley | 604/385.2 |
| 4,795,510 | 1/1989 | Wittrock et al. | 156/64 |
| 4,797,687 | 1/1989 | Holder et al. | 346/1.1 |
| 4,815,660 | 3/1989 | Boger | 239/8 |
| 4,841,307 | 6/1989 | Graham | 346/1.1 |
| 4,849,768 | 7/1989 | Graham | 346/1.1 |
| 4,909,879 | 3/1990 | Ball | 156/164 |
| 4,911,948 | 3/1990 | McIntyre | 427/45.1 |
| 4,955,265 | 9/1990 | Nakagawa et al. | 83/74 |
| 4,969,602 | 11/1990 | Scholl | 239/298 |
| 4,979,380 | 12/1990 | Robbins et al. | 68/205 |
| 4,989,792 | 2/1991 | Claassen | 239/586 |
| 4,995,333 | 2/1991 | Keller et al. | 118/300 |
| 4,996,091 | 2/1991 | McIntyre | 428/113 |
| 5,020,723 | 6/1991 | Crist | 239/11 |
| 5,030,303 | 7/1991 | Cucuzza | 156/164 |
| 5,064,489 | 11/1991 | Ujimoto et al. | 156/164 |
| 5,065,943 | 11/1991 | Boger et al. | 239/298 |
| 5,088,443 | 2/1992 | Hastings et al. | 118/314 |
| 5,124,111 | 6/1992 | Keller et al. | 264/555 |
| 5,145,689 | 9/1992 | Allen et al. | 425/72.2 |
| 5,269,670 | 12/1993 | Allen et al. | 425/72.2 |
| 5,421,941 | 6/1995 | Allen et al. | 156/244.11 |

APPARATUS AND METHODS FOR SELECTIVELY CONTROLLING A SPRAY OF LIQUID TO FORM A DISTINCT PATTERN

This is a divisional application of copending application U.S. Ser. No. 07/991,780, filed on Dec. 16, 1992.

BACKGROUND OF THE INVENTION

This invention relates to apparatus and methods for spraying a liquid on a surface.

Various apparatus and methods are currently used for spraying liquids. One example involves an apparatus having a plurality of nozzles that are connected to a single manifold, which is connected to a single large, central tank of liquid. Generally, the large, central tank of liquid and the manifold are spaced a great distance apart for various reasons, one being a need to separate the tank of liquid from the operating apparatus and personnel operating the apparatus. The large, central tank of liquid is pressurized to assist in delivery of the liquid from the tank to the manifold, and then to the individual nozzles, which are turned on and off to spray the liquid. One problem with this type of apparatus occurs when less than all of the nozzles are operated to spray the liquid. Since the manifold, which feeds all the nozzles, is under a constant pressure, it provides a first mass flow rate of liquid to all of the nozzles which spray the liquid in a desired amount and in a desired pattern. If less than all of the nozzles are operated, the mass flow rate to the remaining nozzles will be increased due to the constant pressure applied to the manifold. Consequently, since the remaining operating nozzles have the liquid supplied to them at a second mass flow rate that is greater than the first, their spray will include a greater amount of liquid and the pattern will be altered. A second example of an apparatus for spraying liquid is similar to the above example except that a like plurality of pumps are connected between the respective plurality of nozzles and the large, central tank of liquid; the manifold being absent. Each pair of an individual pump and individual nozzle have a pair of ports or valves that control the flow of liquid. For example, one port or valve is connected in the supply line leading from the tank of liquid to an individual pump, and a second port or valve is connected in the supply line leading from that individual pump to its respective nozzle. The pumps generally run continuously whether or not liquid is being supplied from the tank. The nozzles may be operated all together, or only groups of the nozzles may be operated. When one nozzle is to spray liquid, the apparatus causes the port or valve between the tank and pump to open to allow liquid to flow to the pump, and then causes the port or valve between the pump and nozzle to open for spraying the liquid. One problem with this type of apparatus occurs when a virtually instantaneous spray of liquid is required at a specific point in time. Because two ports or valves are required to be open, the liquid is not immediately supplied to the nozzle under the requisite pressure to provide a full spray of liquid at the desired time. Any delay in spraying the liquid at the specified time will result in the pattern of spray being out of the desired position or being altered in shape. This problem is particularly undesirable when the surface being sprayed is continuously moving and requires the pattern of spray to be positioned at a desired portion of the surface.

SUMMARY OF THE INVENTION

In one form of the invention, there is provided a method of spraying a liquid in a plurality of patterns on a moving surface that includes the steps of moving a surface having a plurality of references thereon, supplying a plurality of sources of a liquid, providing a plurality of spray devices in fluid communication with respective ones of the plurality of sources of liquid, individually controlling each spray device to spray the liquid at the moving surface to form a plurality of patterns on the moving surface relative to the references, sensing the position of a pattern relative to its respective reference, generating a position signal in response to the position of the pattern, processing the position signal according to a pre-programmed instruction, generating a correction signal when the pattern is out of position, and adjusting the control of selected ones of the spray devices to correctly position a subsequent pattern relative to its reference.

In another form of the present invention, there is provided a method of spraying a liquid in a pattern on a surface that includes the steps of supplying a source of liquid, providing a surface, describing a prescribed location on the surface, forming a spray of the liquid in a pattern relative to the prescribed location, sensing the position of the pattern relative to the prescribed location, generating a position signal in response to the position of the pattern, processing the position signal according to a pre-programmed instruction, generating a correction signal when the pattern is out of position, and adjusting the spray of liquid in response to the correction signal to position a subsequent pattern relative to its prescribed location.

Yet another form of the present invention, there is provided a method of spraying a liquid in a plurality of patterns on a moving surface that includes the steps of moving a surface, directing a plurality of sprays of a liquid at the moving surface, and individually controlling each spray of liquid independently of the other sprays of liquid to form a pattern on the moving surface.

In still yet another form of the present invention, there is provided a disposable absorbent article that includes a layer and an absorbent disposed with the layer, in which the layer and absorbent are joined together by one of the methods of the present invention.

In a further form of the present invention, there is provided a disposable absorbent article that includes a base sheet and an absorbent on the base sheet, in which the base sheet includes at least two layers that are joined together by one of the methods of the present invention. In still a further form of the present invention, there is provided a disposable absorbent article that includes a topsheet, a backsheet, an absorbent between the topsheet and the backsheet, and a layer that is joined to the topsheet by one of the methods of the present invention.

BRIEF DESCRIPTION OF THE DRAWINGS

The above-mentioned and other features of the present invention, and the manner of attaining them will become more apparent and the invention itself will be better understood by reference to the following description of the invention taken in conjunction with the accompanying drawings, wherein.

DEFINITIONS

Within the context of this specification, each term or phrase below will include the following meaning or meanings:

(a) "Disposed" and variations or uses thereof are intended to mean that one element can be integral with another element, or that one element can be a separate structure joined to or connected or placed with or placed near another element.

(b) "Pattern" includes any geometric or non-geometric form that can include, among others, a series of connected or unconnected lines or curves, a series of parallel or non-parallel or intersecting lines or curves, a series of linear or curvilinear lines, or any combinations thereof. The pattern can include a repeating form(s) and/or non-repeating form(s).

(c) "Spray" and variations thereof includes forcefully ejecting liquid, either as a stream, such as swirl filaments, or atomized droplets through an orifice, nozzle, or the like, by means of an applied pressure of air or other gas, by force of gravity, or by centrifugal force. The spraying can be continuous or non-continuous.

(d) "Liquid" includes a substance and/or material that flows and can assume the interior shape of a container into which it is poured or placed.

(e) "Surface" includes any layer, paper, woven, nonwoven, substrate, laminate, composite, or combinations thereof, and can be pervious or impervious.

(f) "Reference" includes structure such as waist or leg elastics, adhesive material, corners or edges of structure, transporting medium such as conveyor belts, visual marks, magnetic marks, color marks, water-based marks, or other marks that can be sensed or measured.

(g) "Connected" includes joining, either directly or indirectly, at least two elements together by mechanical means, electro-mechanical means, optico-electrical means, or any combinations thereof.

DESCRIPTION OF THE INVENTION

Figure 1:
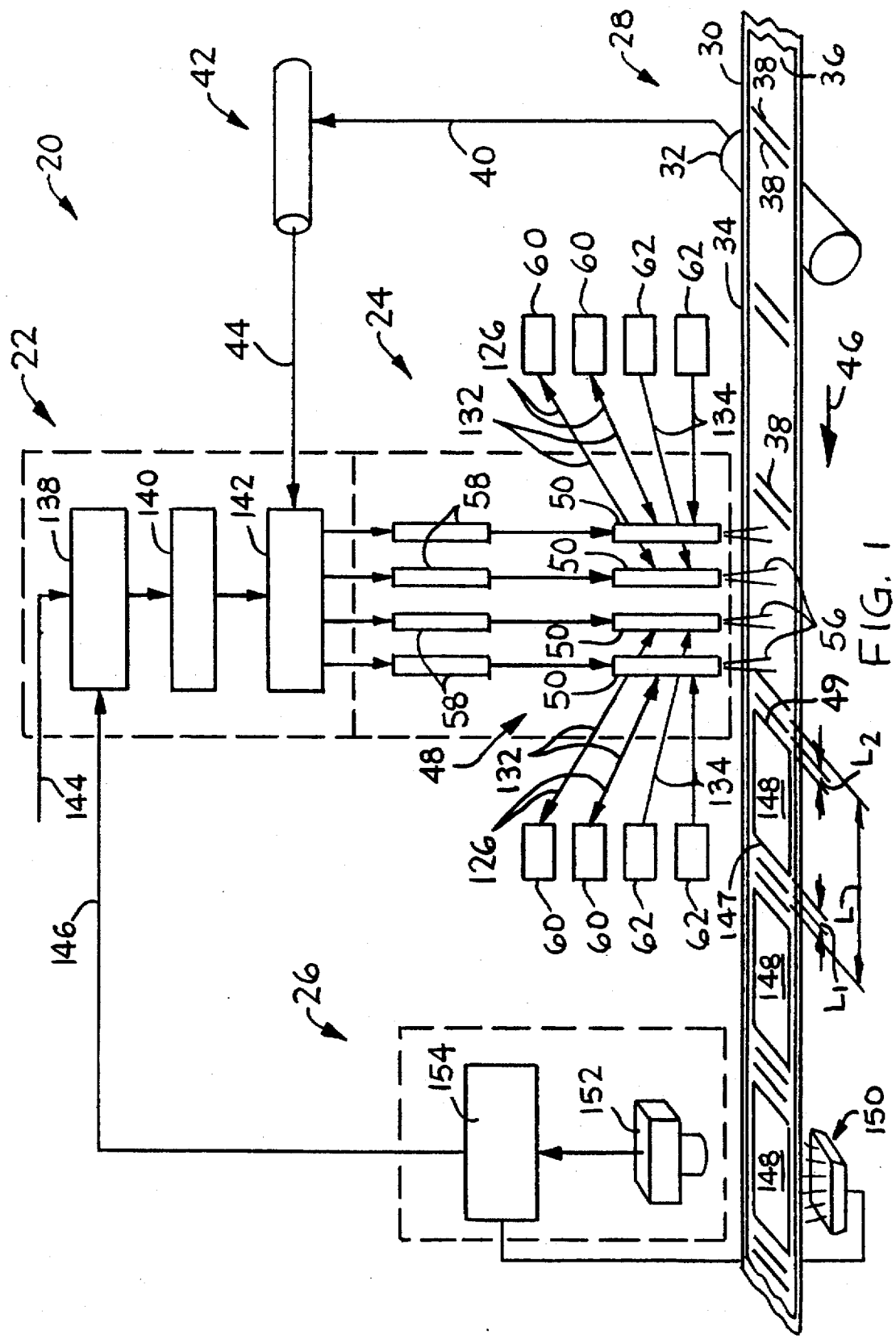
FIG. 1 is a schematic diagram of an apparatus incorporating the principles of the present invention.
Figure 2:
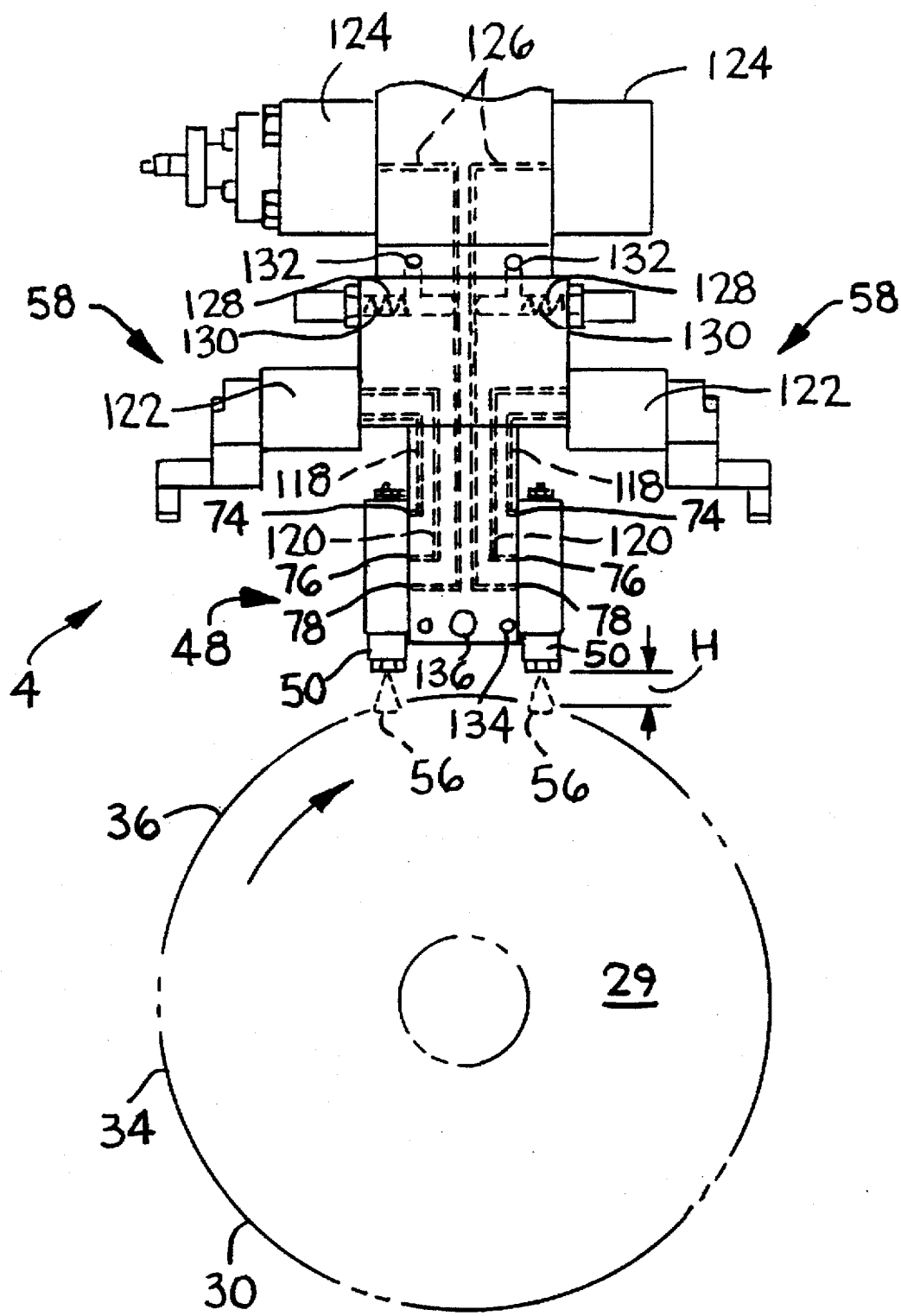
FIG. 2 is a side elevational view of one portion of the present invention.

Referring to FIGS. 1 and 2, there is illustrated apparatus 20 which may be operated according to the principles of the present invention. Apparatus 20 includes programmable control center 22 operatively connected to flow control system 24 which controls the delivery of a liquid, such as a hot melt adhesive in liquid form at application, to be sprayed; and position sensing system 26, which is operatively connected to programmable control center 22, that senses the results or pattern of the spray of liquid and in response thereto generates a signal that is sent to programmable control center 22 for processing. The spray of liquid, which will be referred to as an adhesive spray, can be sprayed in a desired pattern on a moving surface as explained hereafter.

Conveyor system 28 is spaced apart from flow control system 24, and includes conveyor belt 30 (FIG. 1) having a conveyor belt surface 34 that moves continuously by means of conveyor roller 32, and chill roll 29 (FIG. 2) that conveys film 36 at a spaced-apart distance H from flow control system 24. Here, distance H is ¾ inch. Film 36, on which the adhesive is to be sprayed, is carried by conveyor belt surface 34 to flow control system 24. Film 36 can include any type of layer or web of material, such as films of thermoplastic material, a non-woven web of thermoplastic material or a combination of thermoplastic material and natural fibers such as wood pulp fluff fibers, woven webs made of strands of thermoplastic material, natural material such as threads of cotton and the like, or combinations thereof. Although reference numeral 36 will be referred to as a film, the present invention contemplates that reference numeral 36 can include any of these types of layers or webs in the definition of the word "surface". As will be described hereafter in more specific terms, film 36 has the adhesive sprayed on its surface in a specific design or pattern for subsequent placement or joining to another surface.

Before film 36 is conveyed to flow control system 24, it has a plurality of references provided that can be sensed by position sensing system 26. As earlier described, these references include some type of mark, signal, or location that can be sensed, measured, or the like, and in response thereto a signal can be generated by position sensing system 26. In this description, the reference is a plurality of waist elastics 38 that are disposed on film 36 in any suitable manner. One manner of disposing waist elastics 38 is disclosed in U.S. Pat. No. 4,608,115 which issued Aug. 26, 1986, to the assignee of this application and is entitled "Revolving Transfer Roll". U.S. Pat. No. 4,608,115 is incorporated by reference herein. Other apparatus can be used to treat film 36 with other references, such as with different colors, magnetic marks, and the like.

In order to initiate the spray operation at the correct time or correct position, timing mechanism 42 is mechanically coupled to conveyor roller 32 such as, for example, by a belt and pulley assembly represented by line or shaft 40, and operatively connected to programmable control center 22 by line 44. Timing mechanism 42 is a resolver 42, the function of which is to translate one revolution of conveyor roller 32 into one product length L and in response thereto generate an electrical signal to programmable control center 22 via line 44. Product length L is the distance between a centerline of one pair of elastics 38 and a centerline of a second pair of elastics 38 as illustrated in FIG. 1. Resolver 42 is a rotary position transducer that is connected to conveyor roller 32, and produces a position signal that is converted to a digital format for processing by programmable control center 22. One type of resolver 42 can be obtained from Namco Controls of Mentor, Ohio, and has part number CA 150-20000. Resolver 42 can be adjusted such that one rotation of conveyor roller 32 can be any fraction or multiple of a product length L. For example, one rotation of conveyor roller 32 can be translated into one-half a product length or twice a product length, and similarly one-half rotation of conveyor roller 32 can be translated into any fraction or multiple of product lengths L. Line or shaft 40 can also be connected to the apparatus disclosed in the above-mentioned U.S. Pat. No. 4,608,115 which can dispose waist elastics 38 on film 36. Thus, a pair of waist elastics 38 being positioned on film 36 can signal resolver 42 that a product length has been initiated or started, which in turn is processed by resolver 42 into a signal and sent through line 44 to programmable center 22. As mentioned above, in any one product length L, the second waist elastic of one pair of elastics 38 in the downstream direction, which is illustrated by arrow 46, and the first elastic in a subsequent pair of waist elastics 38, form the two waist elastics 38 for that one particular product length L. Other mechanisms may be adapted to be used between film 36 and programmable control center 22 to provide the desired signal to programmable center 22 to begin the spray operation.

Figure 3:
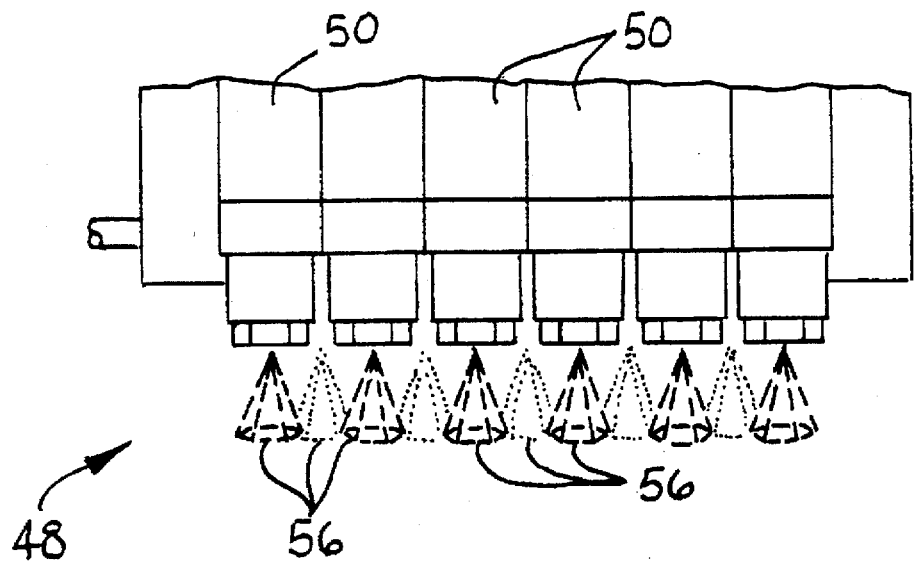
FIG. 3 is a fragmentary side elevational view of a bank of nozzles.
Figure 4:
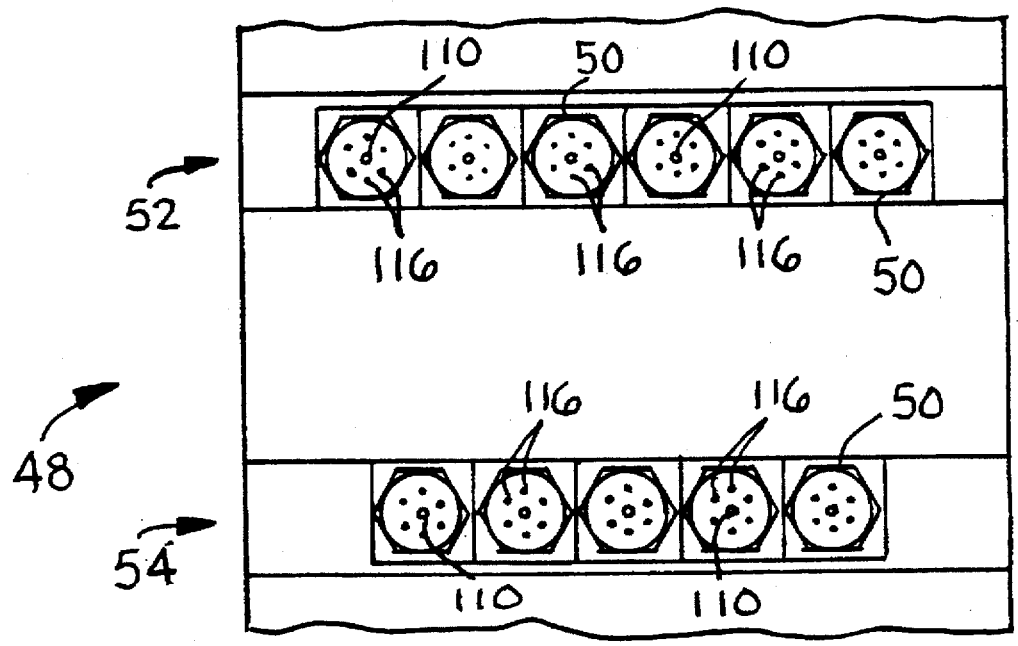
FIG. 4 is a plan view of the bank of nozzles in FIG. 3.

Referring to FIGS. 1–5, flow control system 24 includes bank 48 (FIG. 4) of eleven nozzles 50. The nozzles are in two rows, with six nozzles 50 in row 52 and five nozzles 50 in row 54, in which the two rows of nozzles overlap. In other words, a pair of adjacent nozzles 50 in row 52 (FIG. 4) has their sprays 56 overlapping a spray 56 of a nozzle 50 in row 54, as illustrated in FIG. 3. By offsetting nozzles 50 of row 54 with nozzles 50 of row 52, an uninterrupted spray of liquid can be directed onto film 36. As mentioned earlier, the sprayed liquid is a hot melt adhesive, but the invention contemplates that the liquid can be other types of liquid such as inks, inks of different color, different types of adhesive melts, fiber-forming polymer melts, or any other combinations of desired liquids to be sprayed.

Each nozzle 50 is connected to its own respective solenoid 58 which controls the flow of adhesive to and from that nozzle. Nozzle 50 can be any nozzle suitable for operation with the present invention; one such nozzle is obtainable from ITW Dynatec Co. of Hendersonville, Tenn., and has part number 057B1639, I.D. #A3.

Each solenoid 58 can be any solenoid suitable for operation with the invention; one such solenoid is obtainable from MAC Valves, Inc. of Luixom, Mich., and has model No. 45AL00DDAJ1KG.

Figure 5:
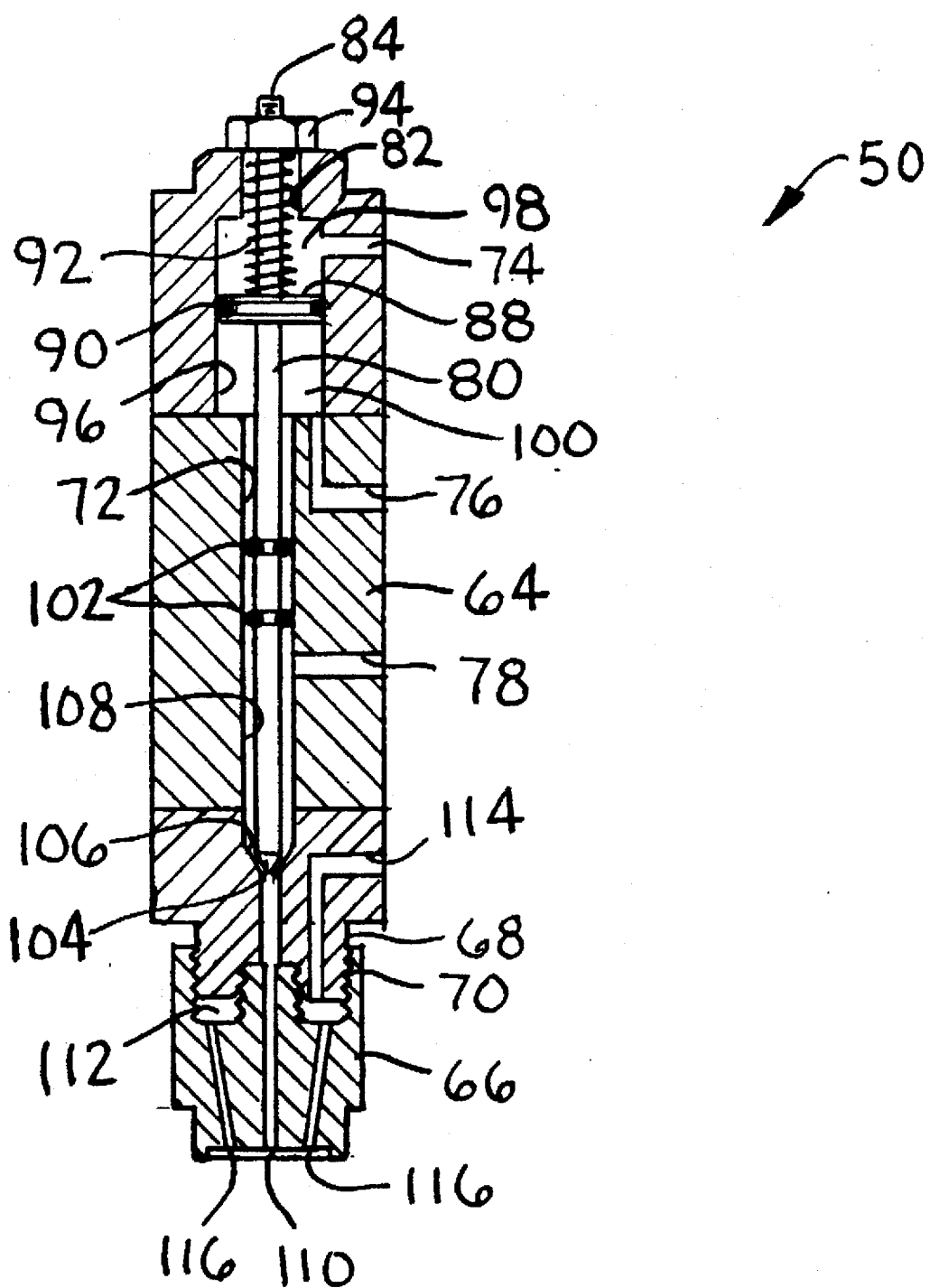
FIG. 5 is a cross-sectional view of a nozzle.

With reference to FIGS. 1, 2, and 5, each nozzle 50 is connected directly to its own source 60 of adhesive and its own source 62 of hot air for spraying and/or swirling the adhesive. Each nozzle 50 includes a main body 64 and cap 66 threadedly joined together by respective threaded surface 68 and threaded surface 70. Body 64 includes a main passage 72 being in fluid communication with air port 74, air port 76, and adhesive inlet 78.

Movably disposed in main passage 72 is pin 80, and disk 88 that is sealed against the inner surface 96 by circular seal 90. Stop-bolt 84 has nut 94 threadedly engaged thereto for adjusting the movement of pin 80 between a closed and stop position in passage 72. Spring 92 is positioned between nut 94 and disk 88 to urge disk 88 downwardly as viewed in FIG. 5. Disk 88 is located between air port 74 and air port 76, and spring 92 urges pin 80 in a downward direction as viewed in FIG. 5. A pair of seals 102 are disposed between pin 80 and main passage 72 below disk 88, and the series of seals 90, 102 create chamber 98 in fluid communication with air port 74, and chamber 100 in fluid communication with air port 76. Chambers 98, 100 are fluidly sealed from one another by seal 90. The lowermost portion of pin 80 includes tapered end 104 that sealingly fits cone-shaped section 106 of main passage 72. Tapered end 104 is illustrated in the open position, and when pin 80 is moved downwardly to seat against cone-shaped section 106, main passage 72 is closed. Between seals 102 and cone-shaped section 106 is adhesive chamber 108 in fluid communication with adhesive inlet 78. Below cone-shaped section 106, main passage 72 continues downwardly toward adhesive opening 110 in cap 66. Cap 66 and main body 64 form therebetween hot air chamber 112 which is in fluid communication with hot air inlet 114 in main body 64 and hot air openings 116.

Referring primarily to FIG. 1 and 2, each solenoid 58 is a three-way valve that is operable between an air-inlet position, an air-outlet position, and an exhaust position in which air flow is exhausted to vacate pressure at air ports 74, 76. A solenoid 58 is connected to a nozzle 50 by air line 118 in fluid communication with air port 74 of nozzle 50, and air line 120 in fluid communication with air port 76 in nozzle 50 (FIG. 5). Air manifold 122 delivers air under pressure to a respective solenoid 58. Air manifold 122 can be supplied with air under pressure by any suitable means, such as by a gear pump.

Adhesive is supplied from a respective source 60 (FIG. 1) to a respective adhesive pump 124 (FIG. 2), which is a obtainable from Acumeter Laboratories of Marlborough, Mass., and has a pump assembly No. 16269.

The flow of adhesive to adhesive pump 124 can be supplied by any suitable means, such as by a gear pump. Each adhesive pump 124 is connected to an adhesive inlet 78 (FIG. 5) of a nozzle 50 by an adhesive supply line 126 and delivers adhesive to its respective nozzle 50 at a constant pressure that is independent of and unaffected by the operation of the other adhesive pumps 124 that deliver adhesive to their respective nozzles 50. Each pump 124 and its respective nozzle 50 includes a pressure-relief chamber 128 that is closed off from adhesive supply line 126 by a spring element 130. When a respective nozzle 50 is in the closed position, adhesive pressure builds up in adhesive supply line 126 until the force of a respective spring element 130 is overcome, thereby opening tank return line 132 (FIG. 2) which delivers the adhesive back to source 60 (FIG. 1). Dedicated to each nozzle 50 is a solenoid 58, adhesive source 60, adhesive pump 124, tank return line 132, and source 62 of hot air (FIG. 1).

Source 62 of air can be supplied by any suitable means, such as by a gear pump, and is delivered by hot air supply line 134 to hot air inlet 114 (FIG. 5) in nozzle 50. A heater cartridge 136 is provided to each nozzle 50 in order to provide heat to the adhesive to increase its flow properties. One such heater cartridge is obtainable from Watlow Electric Manufacturing Company of St. Louis, Mo., and has a part number L7A37-NC12.

With reference to FIG. 1, programmable control center 22 includes computer 138, programmable limit switch 142, and interface 140, such as an RS232 interface, operatively connecting computer 138 and programmable limit switch 142. Computer 138 further includes manual control 144 for manually controlling programmable limit switch 142. Computer 138 receives position signals from position-sensing system 26 via line 146. Computer 138 is a programmable computer, and one such computer is obtainable from Allen-Bradley of Milwaukee, Wis., and is identified as a PLC 5/25 programmable logic controller. Computer 138 is programmed to receive a position signal from position-sensing system 26 and to determine whether an adhesive spray pattern, either the whole pattern itself or only a portion thereof, is correctly positioned on film 36 with reference to waist elastic 38. If the position of the spray pattern does not meet the criteria of the programmed instruction in computer 138, computer 138 will generate a correction signal in response to the adhesive pattern being out of position, and send the correction signal to interface 140.

Interface 140 encodes the correction signal from computer 138 and sends it to programmable limit switch 142, which in turn receives the correction signal and adjusts the operation of any one or more of nozzles 50 to properly position a subsequent adhesive spray pattern on film 36 with reference to waist elastic 38. One such programmable limit switch is obtainable from Namco Controls, an Acme- Cleveland Company, of Mentor, Ohio, and is identified as C&A Programmable Limit Switch No. CA410-23000.

Programmable limit switch 142 will select which nozzles 50 that should be actuated to spray earlier in time or later in time, and also determines whether the duration of spray time should be increased or decreased.

In response to the control signals from programmable limit switch 142, nozzles 50 spray a liquid in a desired pattern 148 (FIG. 1) on film 36. As film 36 moves in the direction of arrow 46, it approaches position-sensing system 26, which includes camera system module 154, camera 152, and ultraviolet light source 150 disposed on an opposite side of film 36 for radiating ultraviolet light against film 36, waist elastics 38, and adhesive patterns 148. A detector such as camera 152 optically senses the position of an adhesive pattern 148 relative to waist elastics 38. For example, camera 152 will optically sense the distance $L_1$, which is the distance between a waist elastic 38 nearest to end edge 147 of adhesive pattern 148, and the distance $L_2$, which is the distance between opposite end edge 149 of adhesive pattern 148 and the nearest waist elastic 38. The present invention contemplates other types of reference points that can be used to determine the position of adhesive pattern 148 relative to waist elastic 38, and as mentioned earlier there are other types of references other than waist elastics 38 that can be used to measure or sense the position of adhesive pattern 148 relative to its prescribed location on film 36. Camera system module 154 receives a signal from camera 152, generates a position signal in response thereto, and sends it via line 146 to computer 138. Computer 138 then processes that position signal and, when adhesive pattern 148 is out of position, generates and sends a correction signal to interface 140, which encodes the signal and sends it to programmable limit switch 142. One such position sensing system is obtainable from the Videk System Division of Eastman Technology, Inc. located in Canadaigua, N.Y.; in which camera system module 154 is identified as model No. RM 1000E, camera 152 is identified as model No. K01313, and light source 150 is identified as model No. K01289.

In the above description, waist elastics 38, which serve as the references for detecting the position of adhesive pattern 148, have been described as being positioned on film 36 before flow control system 24 sprays adhesive on film 36. The present invention contemplates that this sequence can be reversed such that flow control system 24 first sprays the desired adhesive pattern 148, and thereafter waist elastics 38 are disposed on film 36 relative to adhesive pattern 148. Then, the sensing of the position of adhesive pattern 148 on film 36 relative to the references can be the same as described above.

In operation, conveyor system 28 is operated and waist elastics 38 are disposed on film 36, line or shaft 40 begins to operate, and resolver 42 signals programmable limit switch 142 of programmable control center 22 via line 44, as illustrated in FIG. 1. Programmable limit switch 142, which has been preprogrammed with an instruction for each nozzle 50 in bank 48, begins to operate each nozzle 50 to open the nozzle at a preprogrammed time or position to apply spray 56 at a prescribed location on film 36, maintains each nozzle 50 in the open position for a preprogrammed duration of time, and then closes each nozzle 50 at a preprogrammed time.

Since each nozzle 50 operates the same, a description of the operation of one nozzle 50 only will be given. With reference to FIGS. 1, 2 and 5, a pump 124 for a respective nozzle 50 is continuously running to supply adhesive from a source 60 (FIG. 1) via adhesive supply line 126 (FIG. 2) to adhesive inlet 78 (FIG. 5). Similarly, a source 62 is continuously providing air via air line 134 (FIG. 2) to hot air inlet 114 (FIG. 5), hot air chamber 112 and through hot air openings 116. As mentioned earlier, each solenoid 58 is a three-position or three-way valve operating to deliver, from air manifold 122 (FIG. 2), a supply of air to either air port 74 (FIG. 5) or air port 76, or to be positioned at an exhaust position. With a solenoid valve 58 in the closed position, spring 92 (FIG. 5) biases pin 80 downwardly to seat tapered end 104 in cone-shaped section 106 to prevent any flow of adhesive from adhesive inlet 78 and adhesive chamber 108 through adhesive opening 110. Solenoid 58 is activated by a signal from programmable limit switch 142 to open nozzle 50 by supplying air from air manifold 122 to air port 76 in order to create pressure in chamber 100 greater than the pressure in chamber 98 so as to move disk 88 and pin 80 upwardly to unseat taper end 104, thereby permitting adhesive to flow under pressure through adhesive inlet 78, adhesive chamber 108, and through adhesive opening 110 in a spray 56 on film 36 (FIG. 1). As illustrated in FIG. 2, film 36 is delivered by conveyor belt surface 34 over chill roll 29 which is chilled so that the hot adhesive does not melt the film. Heater cartridge 136 (FIG. 2) serves to maintain the adhesive at the proper temperature to maintain it in a state sufficient for spraying.

Programmable limit switch 142, after opening a nozzle 50, is programmed to maintain that nozzle 50 in the open position for a specified period of time at the end of which programmable limit switch 142 activates solenoid 58 to stop the flow of air to air port 76 and to begin a flow of air to air port 74 and chamber 98; this, together with spring 92, moves disk 88 and pin 80 in a downward direction to seat tapered end 104 in cone-shaped section 106, thereby stopping the flow of adhesive through adhesive opening 110. Thereafter, the build-up of adhesive pressure activates spring element 130 in pressure-relief chamber 128 to permit adhesive to flow through tank return line 132 to a source 60.

Programmable limit switch 142 operates each of the nozzles 50 at a preprogrammed time and for a preprogrammed duration that results in adhesive pattern 148, which as illustrated in FIG. 1 is a generally rectangular adhesive pattern. As film 36 with adhesive pattern 148 and waist elastics 38 moves in the direction of arrow 46, position-sensing system 26 activates UV light source 150 and camera 152 to optically sense the position of adhesive pattern 148 relative to waist elastics 38. As described earlier, the position can be measured by length $L_1$ and length $L_2$ (FIG. 1), which are the respective distances between the downstream end edge 147 of adhesive pattern 148 and the nearest adjacent waist elastic 38 and the distance between the upstream end edge 149 of the same adhesive pattern 148 and the nearest adjacent waist elastic 38. Camera 152 sends that measured information to camera system 154 which generates and sends a position signal to computer 138 via line 146. Computer 138, which has been preprogrammed as desired for the specific operation and adhesive pattern design, determines if adhesive pattern 148 is out of position, which may be due to any of several reasons such as the stretching or skewing of film 36, and, if out of position, processes that information according to preprogrammed instructions to generate and send a correction signal to programmable limit switch 142 via interface 140. Programmable limit switch 142 receives the correction signal, which may apply to one or more of nozzles 50, and will controllably adjust the operation of the necessary nozzles 50 to begin the spray operation earlier or later and/or to stop the spray operation earlier or later.

Because each nozzle 50 has its own control solenoid 58, its own source 60 of pressurized adhesive, and its own pressurized source of hot air 62, each nozzle 50 can be quickly operated independently of the other nozzles 50 to provide nearly instantaneous initiation and termination of a spray of adhesive or other liquid. Furthermore, because each nozzle 50 has its own supplies of adhesive and hot air, and is individually controlled by programmable limit switch 142, the turning on or off of more or fewer nozzles does not affect the pressure of the adhesive delivered through other operating nozzles 50, which maintains the mass flow rate of adhesive through a nozzle 50 constant, thereby not affecting a spray 56 and an adhesive pattern 148 made by sprays 56.

Although the invention has been described as spraying adhesive, other combinations of spray operations can be utilized by the present invention. For example, certain nozzles 50 can have one type of adhesive, while other nozzles have a different type of adhesive. Other liquids are contemplated, such as inks, different colored inks, or combinations of inks, adhesives, fiber-forming polymer melts, or any other type of desired liquid that is to be sprayed. If other types and combinations of liquids are to be used, different types of nozzles 50 may be needed to accommodate the different liquids. There also may be a requirement to adjust distance H (FIG. 2) and the flow of hot air from sources 62 (FIG. 1).

Adhesive pattern 148 can be moved, as viewed in FIG. 1, to the left or to the right, up or down, or lengthened or narrowed, or any combination thereof, by programming programmable limit switch 142 and computer 138 with appropriate instructions. Similarly, adhesive pattern 148 can have its design changed, for example, from a rectangular design to an hourglass design, or from a design of non-continuous to continuous lines, or any combinations as earlier described.

Figure 6:
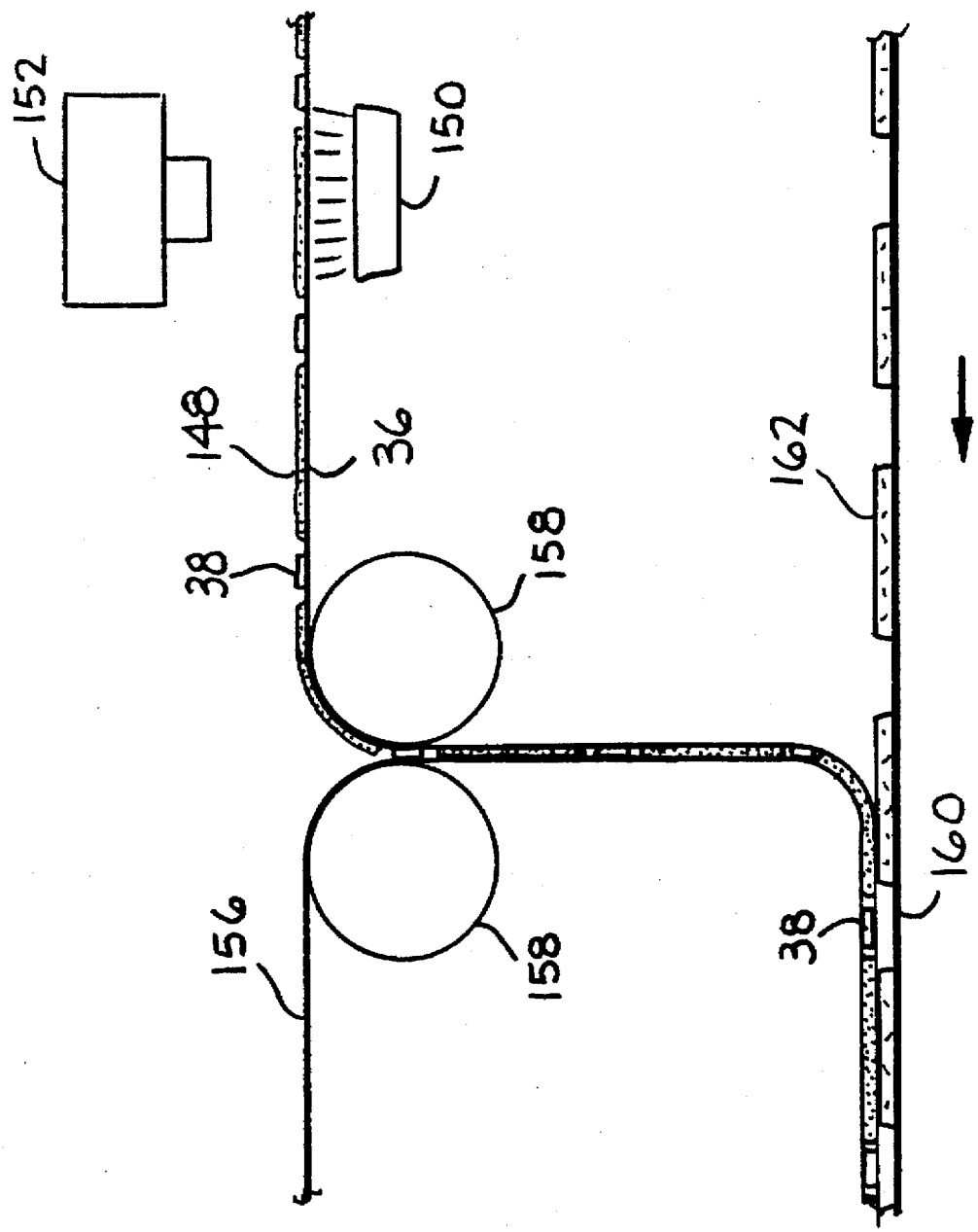
FIG. 6 is a schematic diagram illustrating subsequent handling of a sprayed surface.

After adhesive pattern 148 has been applied to film 36, subsequent handling of film 36, as one example, is illustrated in FIG. 6. Film 36 is adhesively contacted with a second layer, such as nonwoven layer 156, between nip rolls 158 to compress adhesive pattern 148 against nonwoven layer 156. Thereafter, this two-layered composite is positioned on, for example, liquid-permeable liner 160 that has a plurality of absorbents 162 thereon. Absorbents 162 can be all fluff, a blend of fluff and superabsorbent materials, synthetic fibers, or any combinations thereof, and is wrapped in a tissue wrap (not shown) to maintain the integrity of the absorbent material. Thereafter, multiple products can be cut from this continuously moving line in order to form individual absorbent articles having a liquid-permeable liner 160, an absorbent 162, a liquid-impermeable film 36, and a cloth-like nonwoven layer 156. This type of general structure can be used in any number of personal care articles, such as a child's training pant or a baby diaper. A description of two types of child's training pants are disclosed in U.S. Pat. No. 4,940,464, issued Jul. 10, 1990, to the assignee of the present invention, and U.S. patent application Ser. No. 07/809,993, filed Dec. 18, 1991, assigned to the assignee of the present invention; the contents of both being incorporated by reference herein. One design of a baby diaper is disclosed in U.S. patent application Ser. No. 07/757,760, filed Sep. 11, 1991, and assigned to the assignee of the present invention; the contents of which are incorporated by reference herein.

Figure 7:
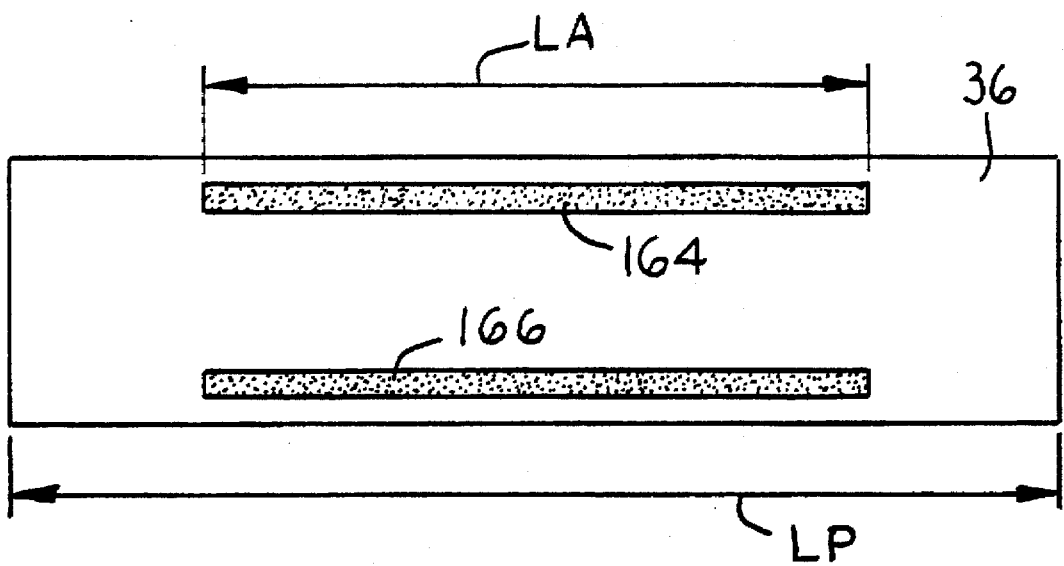
FIG. 7 is a top plan view of a sprayed portion of a moving surface.

As mentioned earlier, liquids, such as the adhesive earlier described, can be sprayed in any number of desired patterns by appropriately programming the present invention. FIG. 7 illustrates film 36 having a pair of generally parallel, spaced-apart adhesive lines 164, 166 that can be sprayed by appropriately programming computer 138 and programmable limit switch 142 to open and close nozzles 50 as desired. For the design in FIG. 7, the outwardly most nozzles 50 of row 52 or row 54 (FIG. 4) are opened and closed at preprogrammed times to spray the straight lines 164, 166 of adhesive.

Figure 8:
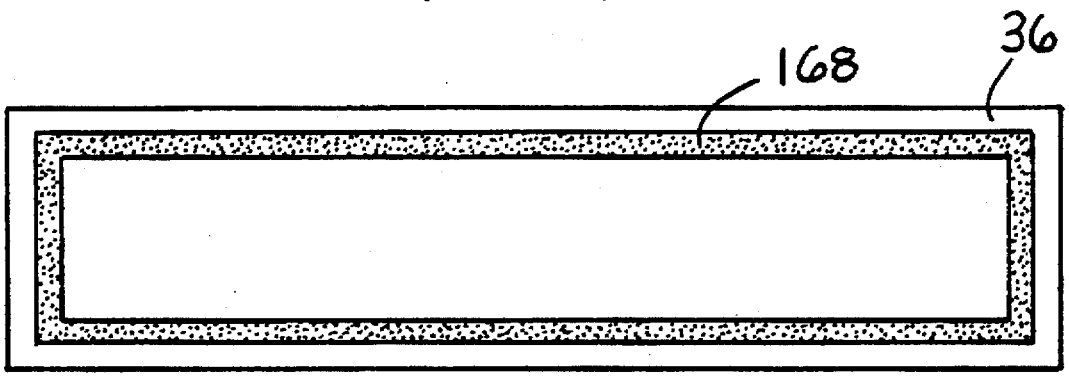
FIGS. 8–11 are similar to FIG. 7 illustrating other spray patterns.

FIG. 8 illustrates a rectangular adhesive pattern 168 on film 36. The width or narrowness of the application of adhesive can be varied by adjusting the height H (FIG. 2), by varying the number of hot air openings 116, varying the adhesive opening 110, varying nozzle type or other combinations.

If desired or necessary, the supply of hot air from any operation of the present invention may be eliminated.

Figure 9:
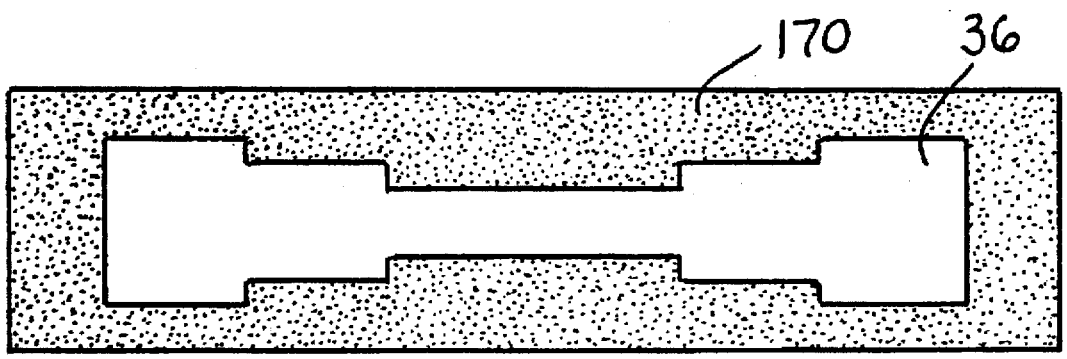

FIG. 9 illustrates adhesive pattern 170 on film 36 that is generally hourglass shaped in which multiple nozzles 50 have been rapidly turned on and off by a preprogrammed instruction in order to provide a stair-step composite spray pattern of liquid that defines the hourglass shape.

Figure 10:
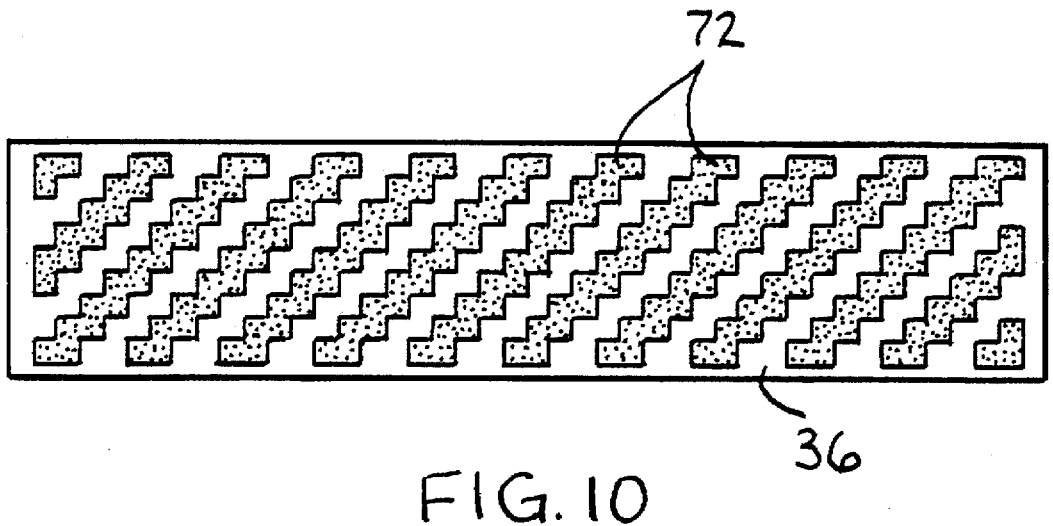

FIG. 10 illustrates yet another adhesive pattern 172 that has rows of adhesive that are generally parallel, spaced apart, stair-stepped, and at an angle with the longitudinal centerline of film 36.

Figure 11:
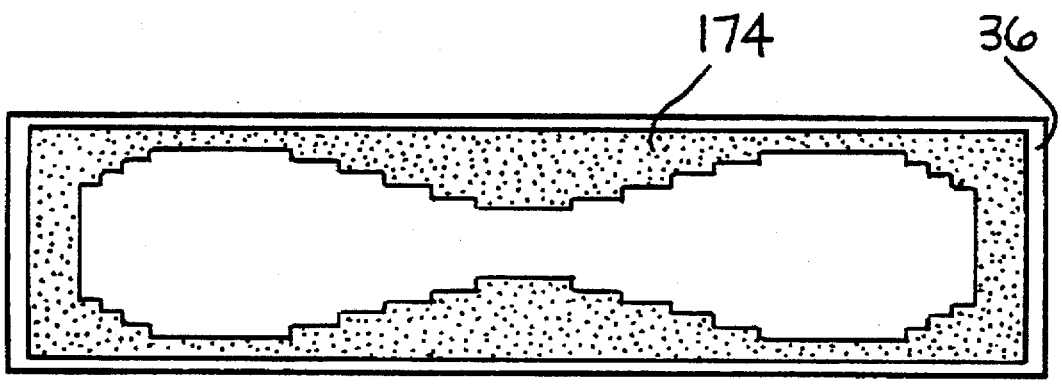

FIG. 11 illustrates yet another adhesive pattern 174.

Although not illustrated, nozzles 50 can be operated to fully cover film 36 with adhesive material.

Figure 12:
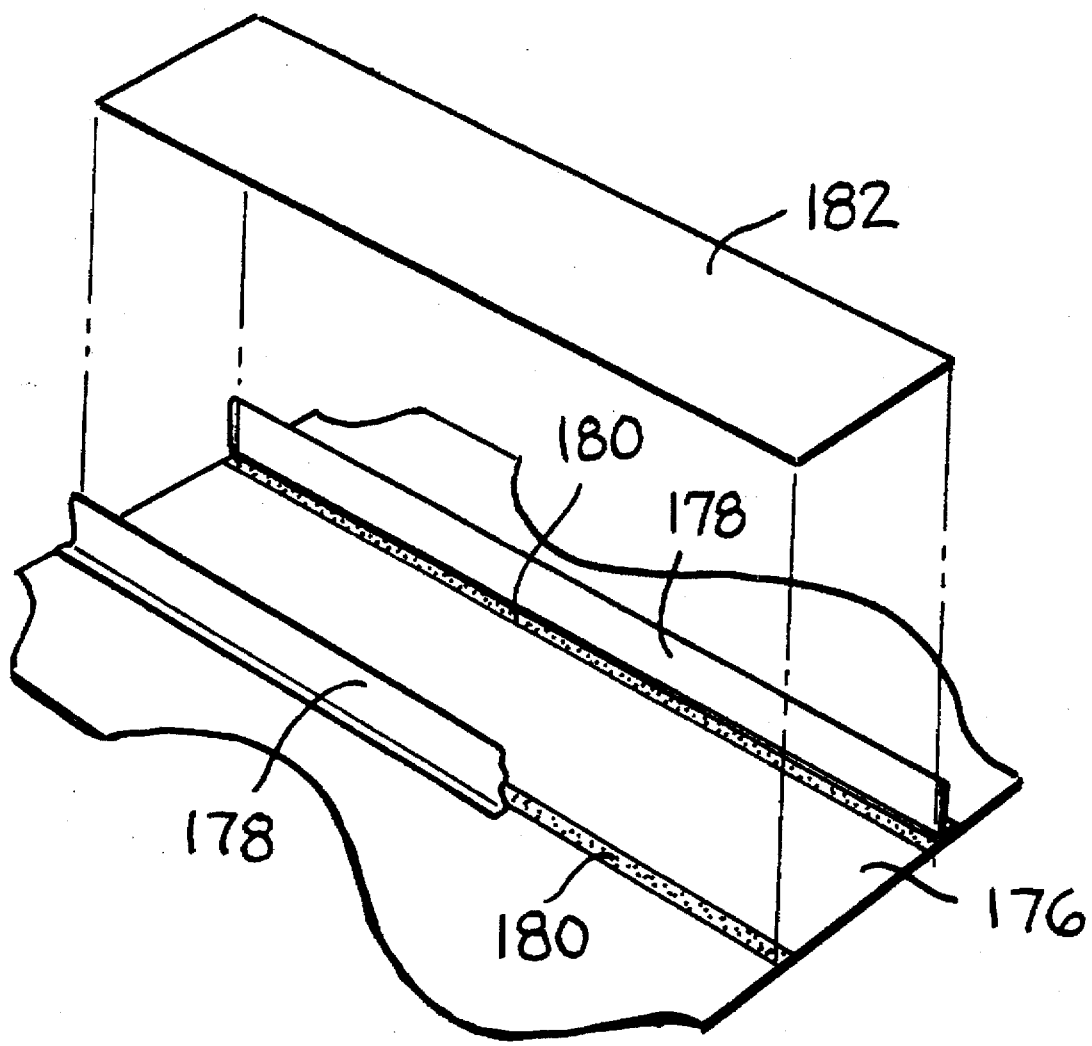
FIG. 12 is an exploded, perspective view of a two-layered composite.

FIG. 12 illustrates joining together two different layers, such as for example, a liquid-permeable liner 176 with a pair of spaced-apart waste containment flaps 178, and layer 182. Two adhesive lines 180 have been sprayed on liner 176 by the present invention. Thereafter, the more narrow layer 182 is positioned on top of adhesive lines 180 to join layer 182 to liner 176.

While the invention has been described in detail with respect to a specific embodiment thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of spraying a liquid in a plurality of patterns on a moving surface, comprising the steps of:

moving a surface having a plurality of references thereon, supplying a plurality of sources of liquid, providing a plurality of spray devices in fluid communication with respective ones of the plurality of sources of liquid, individually controlling each spray device to spray the liquid at the moving surface to form a plurality of patterns on the moving surface relative to respective ones of the references, sensing the position of a pattern relative to its respective reference, generating a position signal in response to the sensed position of the pattern relative to its respective reference, processing the position signal according to a preprogrammed instruction, generating a correction signal when the pattern is out of position relative to its reference, and adjusting the control of selected ones of the spray devices to correctly position a subsequent pattern relative to its reference.

2. The method of claim 1 wherein the step of individually controlling includes moving a pattern relative to its reference.

3. The method of claim 1 wherein the step of individually controlling includes changing a pattern.

4. The method of claim 1 wherein the step of supplying includes supplying at least one source with a liquid different from the other sources.

5. A method of spraying a liquid in a pattern on a surface, comprising the steps of:

supplying a source of liquid, providing a surface, providing a prescribed location on the surface, forming a spray of the liquid in a pattern relative to the prescribed location on the surface, sensing the position of the pattern relative to the prescribed location, generating a position signal in response to the sensed position of the pattern relative to the prescribed location, processing the position signal according to a preprogrammed instruction, generating a correction signal when the pattern is out of position relative to the prescribed location, and adjusting the spray of liquid in response to the correction signal to position a subsequent pattern relative to its prescribed location.

6. The method of claim 5 wherein the step of forming includes forming a plurality of sprays of liquid, and wherein the step of supplying includes supplying a plurality of sources of liquid so that each individual spray of liquid has its own individual source of liquid.

7. The method of claim 6 further comprising the step of individually controlling each spray of liquid independently of the other sprays of liquid.

8. The method of claim 5 further comprising the step of changing a pattern of the spray of liquid.

9. The method of claim 5 further comprising the step of changing a pattern of the spray of liquid.

10. The method of claim 5 further comprising the step of moving the surface continuously, wherein the step of providing includes providing a plurality of prescribed locations on the moving surface, and wherein the step of forming includes forming a plurality of patterns relative to the respective plurality of prescribed locations.

11. The method of claim 10 further comprising the step of changing patterns of the sprays of liquid.

12. The method of claim 10 wherein the step of forming further includes forming a plurality of sprays of liquid, and wherein the step of supplying includes supplying a plurality of sources of liquid such that each individual spray of liquid has its own individual source of liquid.

13. The method of claim 6 wherein the step of supplying a plurality of sprays of liquid includes supplying different liquids to be sprayed.

14. A method of spraying a liquid in a plurality of patterns on a moving surface, comprising the steps of:

moving a surface having a plurality of references thereon, directing a plurality of sprays of a liquid at the moving surface, and individually controlling each spray of liquid independently of the other sprays of liquid to form a plurality of patterns relative to respective ones of the references on the moving surface.

15. The method of claim 14 further comprising the steps of:

sensing the position of a pattern relative to its respective reference, generating a position signal in response to the sensed position of the pattern relative to its respective reference, processing the position signal according to a preprogrammed instruction, generating a correction signal according to the preprogrammed instruction when the pattern is out of position, and adjusting the position of a subsequent pattern relative to its respective reference in response to the correction signal.

16. The method of claim 15 further comprising the step of changing at least one of the patterns on the moving surface.

17. The method of claim 15 wherein the step of directing a plurality of sprays of a liquid includes supplying different liquids.

* * * * *